United States Patent [19]

Rogers et al.

[11] 4,017,505

[45] Apr. 12, 1977

[54] 1-(N-OCTYLTHIOCARBONYL)-2-(4-THIAZOLYL)BENZIMIDAZOLE

[75] Inventors: Edward F. Rogers, Middletown; Wallace T. Ashton, Clark; Richard A. Dybas, Edison, all of N.J.

[73] Assignee: Merck & Co., Inc., Rahway, N.J.

[22] Filed: Oct. 23, 1975

[21] Appl. No.: 625,335

Related U.S. Application Data

[63] Continuation of Ser. No. 467,190, May 6, 1974, abandoned.

[52] U.S. Cl. .......................... 260/302 H; 424/270
[51] Int. Cl.$^2$ ...................................... C07D 417/00
[58] Field of Search ............................... 260/302 H

[56] References Cited

OTHER PUBLICATIONS

Aries, *Chem. Abstracts*, 69:43912r (1968).

*Primary Examiner*—Richard J. Gallagher
*Attorney, Agent, or Firm*—David L. Rose; J. Jerome Behan

[57] ABSTRACT

New benzimidazoles substituted at the 1-position with carbonyl substituents and at the 2-position with a 4-thiazolyl group are effective fungicides and anthelmintics. The compounds as well as processes for their preparation are described along with antifungal and anthelmintic compositions for their use. The 1-position substituent is a hydrocarbon group of from 5 to 12 carbon atoms connected to the carbonyl group through an oxygen or a sulfur atom. The compounds are generally prepared by contacting a 1-unsubstituted benzimidazole with a hydrocarbon radical substituted chloroformate or chlorothiol formate.

1 Claim, No Drawings

1-(N-OCTYLTHIOCARBONYL)-2-(4-THIAZOLYL)BENZIMIDAZOLE

This is a continuation of application Ser. No. 467,190 filed May 6, 1974, now abandoned.

DESCRIPTION OF THE PRIOR ART

Benzimidazoles having a heteroaryl radical in the 2 position have been described in the prior art as anthelmintic and antifungal agents. U.S. Pat. Nos. 3,017,415 and 3,370,957 are illustrative of this prior art. Although these materials are active antifugal agents, the search has continued for substances which are more potent and which are effective against fungi that are non-responsive or weakly responsive to the prior art compounds. In accordance with the present invention there are provided a group of highly active, broad-spectrum antifungal agents.

SUMMARY OF THE INVENTION

This invention relates to new compounds active as fungicides and anthelmintics, and to methods for their use. More specifically, this invention relates to 1-substituted benzimidazoles effective as fungicides. Still more particularly, the invention is directed to novel fungicides comprising compounds described as 1-(hydrocarbon radical) oxycarbonyl-2-(4-thiazolyl)benzimidazole, to compositions containing such compounds and to methods of killing fungi or controlling their growth by the use of such compositions and compounds.

These fungicides are utilized for agricultural application for instance in preventing or minimizing fungus growth on plants, fruits, seeds or soil. In addition, these fungicides are useful in preventing mycotoxicosis, a toxic manifestation of animals which may cause internal lesions, tumors and death which results from ingestion of food contaminated by toxins of fungal origin. These fungicidal agents or materials may also find use in medical therapy such as the treatment of mycotic infections of man and animals with the skin, hair, nails and other areas of the body.

Although many antifungal agents have been described and used heretofore in an effect to control fungi, none are entirely satisfactory and continued losses resulting from fungal attack make the problem of control a serious and lasting one.

It is an object of this invention to provide for novel compounds. It is a further object of this invention to provide novel antifungal agents. It is still a further object of this invention to provide new and improved methods of controlling the growth of fungi. Another object of this invention is to provide compositions useful in the control of fungi in or on food, plants and animals. It is still a further object of this invention to provide a method for controlling and killing fungi with synthetic organic chemicals. Further objects and advantages will become apparent from the following description of the invention.

As used in the description of our invention the expressions "fungicide" and "fungicidal" are intended to encompass control of fungi broadly so as to include the killing of fungi as well as the inhibiting of growth of fungi.

According to the present invention, it has now been found that certain 1 substituted carbonyl benzimidazoles are highly effective antifungal agents. It will be appreciated by those skilled in the art that not all of the compounds defined hereinbelow have exactly the same degree of antifungal activity and it should also be understood that a particular compound of the invention will vary somewhat in activity depending upon the species of fungus subjected to its action.

SUMMARY OF THE INVENTION

The novel antifungal active compounds of this invention are best described by the following structural formula:

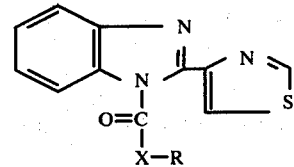

wherein X is oxygen or sulfur and R is a hydrocarbon radical of from 5 to 12 carbon atoms. The hydrocarbon radical so long as it contains the requisite number of carbon atoms, may be of any configuration an may be of any degree of unsaturation including aromatic unsaturations. The generally preferred hydrocarbon radicals are selected from alkyl, cycloalkyl, bicycloalkyl, tricycloalkyl, and aromatic hydrocarbon; loweralkyl substituted with a hydrocarbon group selected from cycloalkyl, bicycloalkyl, tricycloalkyl, or an aromatic hydrocarbon group such that the total carbon content is from 5 to 12 carbon atoms; provided that each of the foregoing groups may be optionally substituted with from 1 to 3 loweralkyl groups and each of the loweralkyl, alkyl, cycloalkyl, bicycloalkyl, or tricycloalkyl groups may optionally contain 1 or 2 unsaturations.

As employed in the instant invention the term "loweralkyl" is deemed to include those alkyl groups containing from 1 to 5 carbon atoms, either of a straight or branched configuration.

The "cycloalkyl" groups include those ring structures containing the appropriate carbon content as above defined with are monocyclic in nature.

The "bicycloalkyl" groups include those ring structures containing the appropriate carbon content as above defined which are bicyclic groups of either the fused ring type as exemplified by decalin, hexahydroindan, bicyclo[3.3.1]octane, and the like; as well as the "spiro" hydrocarbon groups.

The "tricycloalkyl" groups include those ring structures containing the appropriate carbon content as above defined which are tricyclic in nature of the "bridgehead" type as exemplified by adamantane, and the like; as well as other tricyclic groups including the "trifused rings" and "dispiro rings."

The "aromatic" hydrocarbon groups are exemplified by phenyl and naphthyl, as well as by other fully unsaturated rings such as indene, pentalene, azulene, benzocycloheptene and the like.

The preferred compounds of this invention are realized when X is oxygen or sulfur and R is alkyl of from 8 to 10 carbon atoms.

Other preferred compounds are realized when X is oxygen and R is cycloalkyl or loweralkyl substituted with cycloalkyl of from 8 to 12 carbon atoms.

Other preferred compounds are realized when R is bicyclic or loweralkyl substituted with a bicyclic group and said bicyclic group contains from 6 to 10 carbon atoms. As especially preferred bicyclic group is further substituted with loweralkyl groups and is also unsaturated. Said especially preferred group is 6,6-dimethylbicyclo[3.1.1]hept-2-ene-2-ethyl.

The most preferred tricyclic group is the adamantyl group.

As illustrative of the compounds within the scope of this invention which are particularly effective as antifungal agents, there may be mentioned:

1-n-octyloxycarbonyl-2-(4-thiazolyl)-benzimidazole
1-n-nonyloxycarbonyl-2-(4-thiazolyl)-benzimidazole
1-n-decycloxycarbonyl-2-(4-thiazolyl)-benzimidazole
1-n-undecycloxycarbonyl-2-(4-thiazolyl)-benzimidazole
1-n-dodecyloxycarbonyl-2-(4-thiazolyl)-benzimidazole
1-(2-ethyl-1-butoxycarbonyl)-2-(4-thiazolyl)-benzimidazole
1-(2-ethyl-1-hexyloxycarbonyl)-2-(4-thiazolyl)-benzimidazole
1-(3,5,5-trimethyl-1-hexyloxycarbonyl)-2-(4-thiazolyl)-benzimidazole
1-(3,7-dimethyl-1-octyloxycarbonyl)-2-(4-thiazolyl)-benzimidazole
1-(1-methyl-1-undecyloxycarbonyl)-2-(4-thiazolyl)-benzimidazole
1-(2-methyl-1-undecyloxycarbonyl)-2-(4-thiazolyl)-benzimidazole
1-(2-n-butyl-1-octyloxycarbonyl)-2-(4-thiazolyl)-benzimidazole
1-(3-methyl-2-butoxycarbonyl)-2-(4-thiazolyl)-benzimidazole
1-(3-hexyloxycarbonyl)-2-(4-thiazolyl)-benzimidazole
1-(4-decyloxycarbonyl)-2-(4-thiazolyl)-benzimidazole
1-cyclohexylmethoxycarbonyl-2-(4-thiazolyl)-benzimidazole
1-(2-cyclohexylethoxycarbonyl)-2-(4-thiazolyl)-benzimidazole
1-(3-cyclohexyl-1-propoxycarbonyl)-2-(4-thiazolyl)-benzimidazole
1-cyclooctylmethoxycarbonyl-2-(4-thiazolyl)-benzimidazole
1-cycloundecylmethoxycarbonyl-2-(4-thiazolyl)-benzimidazole
1-(1-adamantylmethoxycarbonyl)-2-(4-thiazolyl)-benzimidazole
1(1-cyclohexyl-1-butoxycarbonyl)-2-(4-thiazolyl)-benzimidazole
1(2-ethylcyclohexyloxycarbonyl)-2-(4-thiazolyl)-benzimidazole
1-cyclooctyloxycarbonyl-2-(4-thiazolyl)-benzimidazole
1-cyclododecyloxycarbonyl-2-(4-thiazolyl)-benzimidazole
1-citronellyloxycarbonyl-2-(4-thiazolyl)-benzimidazole
1-(6,6-dimethylbicyclo[3.1.1]hept-2-ene-2-ethoxycarbonyl)-2-(4-thiazolyl)-benzimidazole
1-n-octylthiocarbonyl-2-(4-thiazolyl)-benzimidazole
1-n-decylthiocarbonyl-2-(4-thiazolyl)-benzimidazole
1-benzylthiocarbonyl-2-(4-thiazolyl)-benzimidazole The compounds of this invention may be employed in fungicidal treatment of seeds and crop seed pieces, plants, fruits, cereal grains, vegetables, nuts, bulbs, corms and tubers, flowers and ornamentals,, turf, mushrooms, field crops and soils. These compounds are fungicidally effective against *Ascomycetes*, such as *Erysiphe, Monilinia, Diplodia, Mycosphaerella, Sclerotinia, Sphaerotheca spp.* and the like; *Deuteromycetes*, such as *Septoria, Colletotrichum, Botrytis, Fusarium, Penicillium, Verticillium, Cercospora spp.*, and the like; Fungi Imperfecti, such as *Rhizoctonia, Sclerotium spp.*, and the like; and *Basidiomycetes* such as *Ustilago spp.*, and the like.

These compounds are active against pathogenic fungi that attack wood, which are *Penicillium devaricatum, Ophiostoma pilisera, Stemphylium consortiale* and *Trichoderma lignosum;* and fungi associated with deterioration of paint and varnish coatings, such as *Pullularia pullulans, Aspergillus spp., Penicillium spp., Choetomium globosum* and *Trichoderma viride.*

The 1-substituted benzimidazoles of this invention are also effective against pathogenic fungi such as *Trichophyton spp., Microsporum spp., Cryptococcus spp.*, and *Hormodendrum spp.*

It should be understood that the compounds may be utilized in diverse formulations, solid, including finely divided powders and granular materials as well as liquid, such as solutions, emulsions, suspensions, concentrates, emulsifiable concentrate, slurries and the like, depending upon the application intended and the formulation media desired.

Thus it will be appreciated that compounds of this invention may be employed to form fungicidally active compositions containing such compounds as essentially active ingredients thereof, which compositions may also include finely divided dry or liquid diluents, extenders, fillers, conditioners and excipients, including various clays, diatomaceous earth, talc, and the like, or water and various organic liquids such as kerosene, benzene, toluene and other petroleum distillate fractions or mixtures thereof.

In general, the compounds of this invention are also effective in combating superficial mycoses which attack and are in annoyance to humans such as the fungi which causes athletes foot and ringworm.

When the active agents are employed in preventing topical fungi growth one or more of the compounds may be uniformly distributed in a vehicle that is chemically compatible with the particular compound selected, noninhibiting with respect to the action of the antifungal agent and essentially noninjurious to body tissue under the conditions of use.

It should be understood that the 1-substituted benzimidazoles of the invention may be used in combination one with the other as well as with other fungicidally active materials. For instance, a mixture of 1-substituted benzimidazoles and sorbic acid or its salts, propionic acid or its salts, mycostatin, trichomycin, amphotercin, griseofluvin, undecylenic acid, chlorquinadol, 5,7-dichloro-8-hydroxyquinoline (Vioform), o-phenylphenol, biphenyl, chlorinated phenols, sodium benzoate, dehydroacetic acid and its salts or esters of parahydroxybenzoic acid, such as the methyl and propyl ester (parabens) can be used to give fungicidal effect when used in appropriate concentrations. It is quite clear, too, that the compounds defined according to Formula I above may be used in conjunction with effective antibacterial materials in appropriate instances so as to combine the action of each in such a situation as to be particularly useful, for instance, in applications where the presence of bacteria creates undesirable results alongside the detrimental action of fungi.

Pre-harvest treatment is used for sugar beets and for the treatment of cercospora leaf spot(*Cercospora beticola*). In addition, these compounds are employed in the pre-harvest treatment of soybean pod rot complex, grey mold of grapes and various other fungal diseases of vegetables and field crops. Accordingly, a combination of antifungal and antibacterial agents will be useful in the preparation of germicidal soaps, in the production of cosmetics, and in food, such as beer, cheese, or meat applications.

The growth of various fungi existing in soil is limited or terminates by the addition to the soil of minor quantities of the benzimidazole compounds described.

We have also found that the fungicides of the invention are effective against fungal diseases of plants, and may be effectively used either by direct contact with the foliage or systemically, by introduction through the roots.

With respect to the agricultural uses of the fungicides of this invention, the composition may be applied either pre-harvest or post-harvest, depending upon the particular plant, fruit or vegetable being treated and the particular fungus whose presence is suspected.

Post-harvest treatment of various fruits and vegetables with the compounds of this invention results in the successful treatment of many pathogenic fungi to which the fruit or vegetable succeptible of infection. Examples are citrus fruits (penicillium spp., stem and rot organisms and the like); pome fruit such as apples and pears (*Penicillium expansum, Gloeosporium perennans, Botrytis cinerea* and the like); crown rot complex of pathogens of bananas; potato storage and seed piece planting diseases as well as other fungal infections of other fruits and vegetables.

The compounds of this invention also find utility in the various fungi which attack ornamental plants and turf as well as the treatment of seeds to prevent deterioration due to fungal infection while in storage and after planting but before germination.

The pre-harvest treatment of plants with the fungicides of this invention may be carried out using any of the methods known to those skilled in this art. The instant fungicides may be applied as a solution, suspension or dispersion in water in which the plant or the soil in which it is growing, or both, are thoroughly wetted with said aqueous solution, suspension or dispersion. The compounds may be intimately admixed with an inert solid carrier and "dusted" upon the plants. The solid mixture may also contain other necessary ingredients to insure that the composition remains dispersible in air and remains attached to the plant to which it is applied. Or the compounds may be dissolved, suspended or dispersed in a liquid carrier, such as non-phytotoxic oil or other non-aqueous liquid and sprayed directly upon the plant.

When the instant fungicides are used to treat turf and other grasses, the same application methods as above may be employed.

With post-harvest treatment of crops the fungicide may be applied at any time before comsumption, preferably just after harvesting. For instance the antifungal compound may be applied during initial storage, before or after shipping or during final storage before consumption. The benzimidazoles of this invention may be utilized in a number of ways to protect the crop from fungal damage. The antifungal benzimidazoles may be applied directly to the crop as a solution, emulsion, suspension, dispersion and the like, in which the carrier vehicle may be aqueous or non-aqueous in the form of a suitable, wax, oil, organic solvent and the like. The composition may also contain suitable dispersing agents stabilizing agents or other material to insure the uniform application of the benzimidazole derivative. Also the antifungal agent may be applied to the container of wrapper within which the crop is kept in order to prevent fungal damage. The antifungal agent is applied to the container or wrapper in carriers and waxes which are known to those skilled in the art.

The compounds of this invention are prepared by contacting a 1-unsubstituted-2-(4-thiazolyl)-benzimidazole with a hydrocarbon radical substituted chloroformate or chlorothiolformate wherein the hydrocarbon radical is as defined above. The hydrocarbon substituted chloroformate or chlorothiolformate is prepared by contacting the corresponding alcohol or thiol with phosgene.

The preparation of the hydrocarbon chloroformate or chlorothiolformate is conducted in the absence of moisture due to the fact that the product will decompose in the presence of water. The reaction is optionally carried out in a solvent which preferably is anhydrous. The starting materials are also preferred to be in an anhydrous state whether the reaction is run in the presence of a solvent or not. The use of a solvent is preferred for the operation of this process and when a solvent is used it must be nonreactive with either of the starting materials and the product. Aprotic solvents, that is solvents without a replaceable proton such as those found on hydroxy and amine groups are preferred. Hydrocarbon solvents such as benzene, toluene, xylene and the like; chlorinated hydrocarbon solvents such as methylene chloride, chloroform, and the like, are among the preferred solvents employed for this process.

The reaction is generally carried out by adding to a solution of an excess of phosgene gas the hydroxy starting material or a solution thereof. The reaction is exothermic in nature and external cooling, a ver prolonged period of addition, or both, are helpful in moderating the course of the reaction. The initial phse of the reaction is carried out at from −20° to 20° C during the addition of the hydroxy compound to the phosgene which may take from 5 minutes to 6 hours depending on the degree of cooling and the quantity of reactants involved. Following the addition, the reaction mixture is allowed to remain at from 10 to 50° C for from 1 to 72 hours. Thereafter the reaction is worked up and the product isolated by techniques known to those skilled in this art.

One mole of phosgene is required for each mole of hydroxy compound reacted, however, to assist in the completion of the reaction and to prevent dialkyl carbonate formation generally an excess of up to 5 equivalents of phosgene is employed. It is preferred, however, to use from 1 to 3 excess moles of phosgene over the hydroxy compound. Where the exact quantities of phosgene are difficult to monitor, as when gaseous phosgene is employed, the progress of the reaction may be readily followed by removing aliquots of the reaction mixture, working up the aliquots and analyzing them for their infrared spectrum. The disappearance of the hydroxy absorption of the starting material and the formation of the carbonyl absorption of the product may be followed and the necessity of adding increased quantities of phosgene readily determined.

In certain cases, it is desirable to include in the reaction mixture an acid acceptor such as an organic base preferably pyridine which is present in at least a single molar equivalent to the acid being liberated during the course of the reaction. Where the alcohol substrate contains an unsaturation which is of sufficient reactivity that it will add hydrogen chloride across the unsaturation, the use of the acid acceptor is highly desirable.

The hydrocarbon chloroformate thus prepared is reacted with 2-(4-thiazolyl)-benzimidazole to form the products of structural Formula I. Owing to the reactivity of the chloroformate reagent. The reaction mixture and all of the reagents must be scrupulously dried and maintained as such during the course of the reaction. The reaction may be run in an optional solvent which solvent must not react with the chloroformate reagent. The aprotic solvents previously listed in the description of the preparation of the chloroformate are acceptable for this reaction also. Other solvents may also be employed for this step such as acetonitrile, dimethylformamide, tetrahydrofuran and the like.

During the course of the reaction of the chloroformate or chlorothiolformate reagent with the 1-unsubstituted benzimidazole, there is liberated one mole of hydrogen chloride. It is preferred, to facilitate the isolation of pure product, to remove the liberated hydrogen chloride from the site of reaction by reacting it with a suitable base to form a salt. The base must be present to the extent of at least one molar equivalent. As bases tertiary amines are preferred such as triloweralkylamines exemplified by triethylamine, methyldiethylamine and the like; aromatic amines such as N,N-diethylaniline and the like or heterocyclic amines such as pyridine and the like. Where the base is a liquid which is easily removable at the end of the reaction, the use of a separate solvent may be dispensed with and the base used in such an excess as to become the solvent itself. This technique is especially preferred when pyridine is the acid acceptor. The hydrogen chloride formed during the reaction reacts immediately with the base forming a salt which is removed at the end of the reaction by filtering, dissolving in water or some other technique known to those skilled in this art.

The reaction is run initially at from −10° C to room temperature owing to the exothermic nature of the reaction. When the reaction subsides after a period of from 5 minutes to 1 hour, the reaction mixture is allowed to come to from 20° to 50° C for 1 to 24 hours to complete the reaction. The product is then isolated and purified by techniques well known to those skilled in this art.

A variation of the above procedure is realized when a metal salt, preferably an alkali metal or alkaline earth metal salt of the 2-(4-thiazolyl)-benzimidazole is prepared prior to its reaction with the chloroformate or chlorothiolformate reagent. Such a salt is prepared by using the alkali metal or alkaline earth metal hydride, hydroxide or loweralkoxide using methods well known in this art. By the use of such a salt of the benzimidazole, the reaction will produce rather than hydrogen chloride, an alkali metal or alkaline earth metal chloride. Thus with this technique, the use of the base as described above is not needed and it is only necessary to remove the inorganic salt which is formed directly during the course of the reaction.

The process of this reaction is further demonstrated by the following Examples, which Examples are provided for purposes of illustration and are not intended to limit this invention.

EXAMPLE 1

1-n-Octyloxycarbonyl-2-(4-thiazolyl)-benzimidazole 6.03 G. (0.03 moles) of 2-(4-thiazolyl)-benzimidazole is suspended in 50 ml. of pyridine and 6.35 g. (0.033 moles) of n-octyl chloroformate is added maintaining the temperature at 25° C. A clear solution is initially formed which is rapidly followed by the precipitation of pyridine hydrochloride. The reaction mixture is stirred overnight at room temperature, filtered to remove the pyridine hydrochloride and the filtrate evaporated to dryness in vacuo. Ice is added to the gummy residue whereupon it solidifies and is filtered. The solid material is dissolved in methylene chloride and washed with saturated sodium chloride solution. The methylene chloride is dried, and evaporated to dryness in vacuo affording 9.50 g. (89%) of 1-n-octyloxycarbonyl-2-(4-thiazolyl)-benzimidazole, melting point 66° to 67.5° C.

EXAMPLE 2

1-(3-Hexyloxycarbonyl)-2-(4-thiazolyl)-benzimidazole 28.3 G. (0.172 moles) of 3-hexyl chloroformate is added dropwise with protection from moisture to a stirred suspension of 33.1 g. (0.165 moles) of 2-(4-thiazolyl)-benzimidazole in 200 ml. of anhydrous pyridine. The 3-hexyl chloroformate is added over a period of 20 minutes during which time the reaction mixture initially becomes a clear solution followed by the precipitation of pyridine hydrochloride. The reaction mixture is stirred overnight at room temperature filtered to remove pyridine hydrochloride which is washed with some additional anhydrous pyridine and the combined filtrates and washings evaporated to dryness in vacuo. An oil is obtained which is dissolved in 300 ml. of methylene chloride and filtered. The filtrate is washed twice with a 250 ml. of 0.25 N-hydrochloric acid containing ice followed by a washing with 200 ml. of saturated sodium bicarbonate solution. The methylenechloride is dried, treated with charcoal, filtered and evaporated to dryness in vacuo affording 39.2 g. of an orange oil which solidified on standing. The solid material is recrystallized from hexane affording 33.5 g. (62%) of 1-(3-hexyloxycarbonyl)-2-(4-thiazolyl)-benzimidazole melting point 79.5 to 81° C.

EXAMPLE 3

1-(2-Ethyl-1-butoxycarbonyl)-2-(4-thiazolyl)-benzimidazole 17.9 G (0.108 moles) of 2-ethyl-1-butyl chloroformate is added dropwise with protection from moisture to a stirred suspension of 21.7 (0.108 moles) of 2-(4-thiazolyl)-benzimidazole in 150 ml. of pyridine. The addition is carried out over a period of 35 minutes after which the reaction mixture is stirred overnight at room temperature. The reaction mixture is filtered and the filtrate evaporated to dryness in vacuo. The gummy residue is treated with 250 ml. of methylene chloride, filtered and washed twice with 250 ml. of 0.25 N-hydrochloric acid containing ice and 200 ml. of saturated sodium bicarbonate solution. The methylene chloride is dried and evaporated to dryness in vacuo affording 23.8 g. (67%) of a yellow-orange residual oil which is purified by column chromatography, the extract of which thin layer chromatography demonstrates to be pure 1-(2-ethyl-1-butoxycarbonyl)-2-(4-thiazolyl)-benzimidazole.

EXAMPLE 4

1-(1-Cyclohexyl-1-butoxycarbonyl)-2-(4-thiazolyl)-benzimidazole 28.3 G. (0.129 moles) of 1-cyclohexyl-1-butyl chloroformate is added over a period of 20 minutes at a temperature of 20° C to a stirred suspension of 25.1 g. (0.125 moles) of 2-(4-thiazolyl)-benzimidazole and 200 ml. of pyridine. A clear solution initially results which is followed by the precipitation of pyridine hydrochloride. The reaction mixture is then stirred for 16 hours at room temperature filtered and the filtrate evaporated to dryness in vacuo. The product is extracted from the residue with 250 ml. of methylene chloride which is filtered and the filtrate washed twice with 250 ml. of 0.25 N-hydrochloric acid and 200 ml. of saturated sodium bicarbonate solution. The methylene chloride is dried, treated with charcoal, filtered and evaporated to dryness in vacuo. The residual oil is chromatographed on a column of silica gel eluting with benzene affording 21.6 g. (45%) of a pale yellow viscous oil. Thin layer chromatography demonstrates that the oil is pure material which analyzes as 1-(1-cyclohexylbutoxycarbonyl)-2-(4-thiazolyl)-benzimidazole.

EXAMPLE 5

1-Benzylthiocarbonyl-2-(4-thiazolyl)-benzimidazole 17.0 G. (0.091 moles) of benzylthiocarbonyl chloride is added dropwise under anhydrous conditions over a period of 25 minutes to a stirred suspension of 18.3 g. (0.091 moles) of 2-(4-thiazolyl)-benzimidazole in 140 ml. of pyridine. All of the solid material dissolved before the completion of the addition. When the addition is complete, precipitation of pyridine hydrochloride commences. The reaction mixture is stirred at room temperature for 18 hours, filtered and the pyridine solution evaporated to dryness in vacuo. The residue is dissolved in 250 ml. of methylene chloride filtered and the filtrate washed twice with 250 ml. of 0.25 normal hydrochloric acid and 200 ml. of saturated sodium bicarbonate solution. The methylene chloride is dried, treated with charcoal, filtered and evaporated to dryness in vacuo affording a solid material which is recrystallized from toluene affording 14.3 g. (45%) of 1-benzylthiocarbonyl-2-(4-thiazolyl)-benzimidazole, melting point 122° to 123° C.

EXAMPLE 6

1-Cyclooctyloxycarbonyl-2-(4-thiazolyl)-benzimidazole 10.0 G. (0.05 moles) of 2-(4-thiazolyl)-benzimidazole is suspended in 75 ml. of pyridine and 9.5 g: (0.05 moles) of cyclooctyl chloroformate is added dropwise over a period of 25 minutes. The reaction mixture is allowed to stir overnight at room temperature with protection from moisture. The reaction mixture is filtered and the filtrate evaporated to dryness in vacuo. The residue is dissolved in methylene chloride and washed with an excess of dilute hydrochloric acid and dilute sodium bicarbonate. The methylene chloride is dried and evaporated to dryness affording 14.1 g. of viscous residue which thin layer chromatography indicates to be pure material and which analyzes as 1-cyclooctyloxycarbonyl-2-(4-thiazolyl)-benzimidazole. Column chromatography on silica gel affords a solid product melting point 85° to 88° C.

EXAMPLE 7

1-(6,6-Dimethylbicyclo[3.1.1]hept-2-ene-2-ethoxycarbonyl)-2-(4-thiazolyl)-benzimidazole 23.4 G. (0.1 mole) of 6,6-dimethylbicyclo[3.1.1]hept-2-ene-2-ethyl chloroformate is added dropwise over a period of 30 minutes to a stirred suspension of 20.1 g. (0.1 mole) of 2-(4-thiazolyl)-benzimidazole in 150 ml. of pyridine maintaining the reaction in anhydrous condition. The reaction mixture, protected from moisture, is allowed to stir overnight at room temperature, filtered and the filtrate evaporated to dryness in vacuo. The residue is dissolved in methylene chloride and filtered. The filtrate is washed successively with dilute hydrochloric acid, water, dilute sodium bicarbonate solution and finally with water. The methylene chloride is dried and evaporated to dryness in vacuo. 30.8 G. of a viscous residue is obtained which is digested with hexene affording pure 1-6,6-dimethylbicyclo[3.1.1]hept-2-ene-2-ethoxycarbonyl)-2-(4-thiazolyl)-benzimidazole, as a solid melting point 74° to 75° C.

EXAMPLE 8

1-Citronellyloxycarbonyl-2-(4-thiazolyl)benzimidazole 11.0 Grams (0.05 moles) of citronellyl chloroformate is added over a period of ½ hour to a stirred suspension of 10 grams (0.05 moles) of 2-(4-thiazolyl)-benzimidazole and 75 ml. of pyridine at room temperature. The reaction mixture is stirred overnight at room temperature protected from moisture. The solid material is filtered, washed with pryidine and the filtrate and washings evaporated to dryness in vacuo. The residue is dissolved in methylene chloride and the solution washed successively with dilute cold hydrochloric acid, cold water, cold dilute sodium bicarbonate solution and water. The methylene chloride is dried, evaporated to dryness in vacuo affording 16.6 grams of a viscous oil. The oil is chromatographed on a column of silica gel eluting with hexane affording 14.6 grams (76%) of an oil which thin layer chromatography reveals to be pure material and which analyzes as 1-citronellyloxycarbonyl-2-(4-thiazolyl)benzimidazole.

EXAMPLE 9

1-n-Octylthiocarbonyl-2-(4-thiazolyl)-benzimidazole

249 G. (1.19 moles) of n-octylthiocarbonyl chloride is added dropwise over a period of 20 minutes to a stirred suspension of 240 g. (1.19 moles) of 2-(4-thiazolyl)-benzimidazole and 2400 ml. of pyridine; a slight heat rise is evidenced. The reaction mixture is stirred at room temperature for 19 hours, filtered and the solid material washed with methylene chloride. The combined filtrate and washings are evaporated to dryness in vacuo. The residue is mixed with 2000 ml. of methylene chloride and filtered. The solid material is washed with methylene chloride and the combined filtrate and washing are wased twice with water, 3 times with cold 0.25 normal hydrochloric acid (5000 ml. total volume), once with saturated cold sodium bicarbonate and twice with water. The methylene chloride is dried, evaporated to dryness in vacuo affording a syrupy oil which crystallizes under vacuum. The solid material is dissolved in 3 liters of hexane and filtered and the hexane evaporated to a small volume and diluted with petroleum ether to a volume of 3000 ml. whereupon crystallization results. The solid material is filtered and washed with cold petroleum ether affording 219.8 g. (54%) of pure 1-n-octylthiocarbonyl-2-(4-thiazolyl)-benzimidazole, melting point 58° to 59° C.

EXAMPLE 10

1-Cycloundecylmethoxycarbonyl-2-(4-thiazolyl)-benzimidazole 20.3 G. (0.082 moles) of cycloundecylmethyl chloroformate is added dropwise at room temperature to 16.4 g. (0.082 moles) of 2-(4-thiazolyl)-benzimidazole suspended in 200 ml. of pyridine. The temperature rises spontaneously to 35° C and the reaction mixture is then stirred overnight at room temperature, filtered and the filtrate evaporated to dryness in vacuo. The residue is treated with methylene chloride and washed 3 times with 2.5N hydrochloric acid and twice with water. The methylene chloride is treated with charcoal, filtered and evaporated to dryness in vacuo affording 25 g. of an oil which solidifies on standing and is recrystallized from hexane affording 20 g. of 1-cycloundecylmethoxycarbonyl-2-(4-thiazolyl)-benzimidazole, melting point 86° to 87° C.

PREPARATION 1

3-Hexyl chloroformate 20.4 G. (0.2 moles) of 3-hexanol is added dropwise under anhydrous conditions to 345 ml. (0.4 moles) of 12.5% phosgene in benzene with stirring and cooling in an ice bath. The addition is complete in 2 hours and 15 minutes and the temperature is allowed to warm to room temperature and the reaction mixture is stirred overnight. Gaseous nitrogen is passed through the solution for several hours to remove the excess phosgene and hydrogen chloride. The reaction mixture is then evaporated to dryness in vacuo affording 28.3 g. (86%) of a colorless oil which infrared analysis indicates to have a strong carbonyl band and no hydroxy band. The oil is used as is in subsequent reactions.

PREPARATION 2

2-Ethyl-1-butyl chloroformate 20.4 G. (0.2 moles) of 2-ethyl-1-butanol is added dropwise under anhydrous conditions to 250 ml. (0.4 moles) of 17.2% phosgene solution in benzene with stirring in an ice bath. The addition is complete in 70 minutes and the solution is allowed to gradually warm to room temperature and stirred for 16 hours. The excess phosgene and hydrogen chloride are removed with a stream of nitrogen and the residual solution evaporated to dryness in vacuo affording 17.9 g. (54%) of a light yellow oil which IR demonstrates having a strong chloroformate band and no hydroxy. The oil is used as is in further reactions.

PREPARATION 3

1-Cyclohexyl-1-butyl chloroformate

To 224 ml. (0.26 moles) of 12.5% phosgene in benzene at ice bath temperatures under anhydrous conditions is added dropwise 20.3 g. (0.13 moles) of 1-cyclohexyl-1-butanol. The addition takes one hour and the reaction mixture is allowed to gradually warm to room temperature and stirred for 3 days. The excess phosgene and hydrogen chloride are removed by a stream of nitrogen and the solution evaporated to dryness in vacuo affording 28.3 g. (99%) of a pale yellow oil which infrared analysis demonstrates to be 1-cyclohexyl-1-butyl chloroformate.

PREPARATION 4

Benzylthiocarbonyl chloride

A mixture of 12.4 g. (0.1 moles) of benzyl mercaptan and 7.9 g. (0.1 moles) of pyridine are added dropwise with stirring at 5° C to 125 ml. (0.2 moles) of 17.2% phosgene solution in benzene. The reaction mixture is stirred in an ice bath during the addition and for 1 hour thereafter whereupon a solid material begins to precipitate. The reaction mixture is stirred at room temperature for 3 days and filtered and the solution treated with a stream of nitrogen to remove the excess phosgene. The solution is evaporated to dryness in vacuo affording 17.0 g. (91%) of a light yellow oil which infrared analysis demonstrates to be benzylthiocarbonyl chloride.

PREPARATION 5

Cyclooctyl chloroformate 6.4 G. (0.05 moles) of cyclooctanol and 63 ml. (0.1 mole) 17.2% phosgene in benzene are combined according to the procedure of preparation 3 affording cyclooctyl chloroformate as an oil which is used without further purification in subsequent reactions.

PREPARATION 6

6,6-Dimethylbicyclo[3.1.1]hept-2-ene-2-ethyl chloroformate 16.6 G. (0.1 mole) of 6,6-dimethylbicyclo-[3.1.1]hept-2-ene-2-ethanol and 7.9 g. (8.1 ml., 0.1 mole) of pyridine are thoroughly mixed and added dropwise at 10° C to 125 ml. (0.2 moles) of 17.2% phosgene and benzene over a period of 20 minutes. A white precipitate of pyridine hydrochloride forms immediately. The reaction mixture is stirred in the cold for one hour and at room temperature overnight. A stream of nitrogen is passed through the mixture to remove the excess phosgene and the solution is filtered. The filtrate is evaporated to dryness in vacuo affording 23.4 g. (quantitative yield) of 6,6-dimethylbicyclo[3.1.1]hept-2-ene-2-ethyl chloroformate which infrared analysis indicates to be pure material.

PREPARATION 7

Citronellyl chloroformate 8.0 G. (0.05 moles) of citronellol, 3.95 g. (0.05 moles) of pyridine and 65 ml. (0.1 mole) of 16.6% phosgene in benzene are combined according to the procedure of preparation 6 affording an oil which analyzes from infrared spectroscopy as pure citronellyl chloroformate.

PREPARATION 8 n-Octylthiocarbonyl chloride

180 G. (1.23 moles) of 1-octanethiol and 97.2 g. (1.23 moles) of pyridine are added dropwise over one hour to 2000 g. of 12.5% phosgene in benzene maintaining the temperature at from 10° to 12° C with an ice water bath. The reaction mixture is allowed to warm to room temperature and stirred for 21 hours. The reaction mixture is filtered, washed with anhydrous benzene, concentrated to a small volume, filtered and concentrated again to an oil which infrared spectroscopy indicates is pure n-octylthiocarbonyl chloride.

PREPARATION 9

Cycloundecylmethyl chloroformate

21 G. (0.114 moles) of cycloundecylmethanol is added dropwise to a cold solution of 12.5% phosgene in benzene according to the procedure of preparation 3 affording 28.0 g. of an oil which infrared spectroscopy indicates to be pure cycloundecylmethyl chloroformate.

When the compounds of this invention are employed in compositions useful for the destruction of fungi or the prevention of the growth of fungi, the active ingredient is present to an extent which depends greatly upon the method of application of the anti-fungal agent. Concentrations ranging from 0.00001 to 1% by weight may be employed.

Very dilute concentrations of the active ingredient, 0.00001 to 0.01% by weight, are generally employed where a great deal of the composition is to be applied. This is exemplified in the agricultural area wherein the benzimidazole is dissolved or suspended in water which is sprayed onto a field of agricultural crops. The watering generally is part of the normal watering which the plant requires. Since large quantities of water is required, the concentration of antifungal agent may be very low. Higher concentrations, 0.01 to 1% by weight of the antifungal agent are employed for most other applications such as dusts and dispersible oils in the agricultural field and topical creams and ointments in the pharmaceutical area.

The above concentrations of active ingredient are descriptive of those compositions which are to be applied directly to the site of fungal infection or suspected fungal infection. However, it may be desired to provide for an intermediate composition of the compounds of this invention wherein the active ingredient is present to the extent of from 1 to 90% by weight. The remaining ingredients are auxilliary agents such as fillers, excipients, binders or other inert ingredients necessary to maintain the integrity of the composition. This higher concentration composition is further diluted with the proper diluent for the particular contemplated use prior to such use. The dilution brings the concentration of the active ingredient to that desired or necessary for the particular use to which the antifungal composition is to be put.

Compositions containing the active ingredient of structural formula I are active against various fungi when such composition is applied to an area, plant or animal in which fungal growth is present or suspected.

In one such example in the agricultural area an aqueous solution containing 5% acetone and 7.5, 15 or 30 parts per million (ppm) adjusted on a molar basis to the intermediate 2-(4-thiazolyl)-benzimidazole of the active compound were applied as a spray to young bean plants which had been previously inoculated with powdery mildew (*Erysiphe Polygoni*). Other plants were left untreated as controls, The fungi on the plants were then allowed to incubate for from 7 to 10 days. The plants were then evaluated on a scale of from 0 to 10 with 0 being no fungal infection and 10 being complete fungal infection. The following is a summary of the results.

| COMPOUND | | MOLAR ADJUSTED DEGREE OF FUNGAL INFECTION AT CONCENTRATION(PPM) | | |
|---|---|---|---|---|
| | | 7.5 | 15 | 30 |
| A. | 1-(n-octylthiocarbonyl)-2-(4-thiazolyl)-benzimidazole | 0.83 | 0.46 | 0.08 |
| B. | 1-cycloundecylmethoxycarbonyl-2-(4-thiazolyl)-benzimidazole | 0.7 | 0.4 | 0.2 |
| C. | 1-(n-decyloxycarbonyl)-2-(4-thiazolyl)-benzimidazole | 1.1 | 0.51 | 0.11 |
| D. | 1-(6,6-dimethylbicyclo[3.1.1]-hept-2-ene-2-ethoxycarbonyl)-2-(4-thiazolyl)-benzimidazole | 2.0 | 0.75 | 0.11 |
| E. | 1-(3-hexyloxycarbonyl)-2-(4-thiazolyl)-benzimidazole | 3.4 | 1.8 | 0.2 |
| F. | Control | 10.0 | 10.0 | 10.0 |

When the compounds of this invention are intended for topical use such as in a cream or ointment, a base therefor is employed in which the active compound is present at a concentration of from 0.01 to 15% preferably from about 0.5 to 10% (percentages are by weight).

In addition to their antifungal activity the compounds of this invention have significant activity as anthelmintics thus being useful in the treatment of helminthiasis in animals. The disease or group of diseases described generally as helminthiasis is due to infestation of the animal body with parasitic worms known as helminths. Helminthiasis is a prevalent and serious economical problem in domesticated animals such as swine, sheep, cattle, goats, dogs and poultry. Among the helminths, the group of worms described as nematodes causes widespread and ofter serious infection in various species of animals. Certain species of nematodes also lead to troublesome infections in humans, particularly in the tropical climates. The most common genera of neomatodes which infect the animals referred to above are Haemonchus, Trichostrongylus Ostertagia, Nematodirus, Cooperia, Bunostomum, Oesophagostomum, Chabertia, Trichuris (whipworm), Ascaris, Capillaria, Heterakis and Ancylostoma. Certain of these, such as Trichostrongylus, Nematodirus and Cooperia, attack primarily the intestinal tract while others, such as Haemonchus and Ostertagia, are more prevalent in the stomach. The parasitic infections known as helminthiasis lead to anemia, malnutrition, weakness, weight loss, severe damage to the walls of the intestinal tract and, if left untreated, often result in death of the infected animals. The compounds of this invention have unexpectedly high activity against these helminths.

When used as anthelmintic agents, they may be administered orally in a unit dosage form such as a capsule, bolus, tablet or as a liquid drench. The drench is normally an aqueous suspension or dispersion of the active ingredient together with a suspending agent such as bentonite and a wetting agent or like excipient. Generally the drenches also contain an antifoaming agent. The capsules and boluses comprise the active ingredient admixed with a carrier vehicle such as starch, talc, magnesium stearate, or dicalcium phosphate. When the anthelmintic is to be administered via the animal feedstuff, it is intimately dispersed in the feed to the extent of from 0.1 to 5% by weight or else used as a top dressing or in the form of pellets with from 1 to 20% by weight of the active ingredient which are then added to the finished feed. Alternatively, the anthelmintic compounds of this invention may be administered to animals by intraruminal, intramuscular and intratracheal injection, in which event the benzimidazole is dissolved or dispersed in a liquid carrier vehicle.

The optimum amount of the active agent to be employed for best results will, of course, depend upon the particular benzimidazole employed, the species of animal to be treated and the type and severity of helminth infection. Generally, good results are obtained with the compounds of this invention by the oral administration of from about 5 to 125 mg. per kg. of animal body weight, such total dose being given at one time or in divided doses over a relatively short period of time such as 1–2 days. With the preferred compounds of the invention, excellent control of helminthiasis is obtained in domesticated animals by administering from about 10 to 70 mg. per kg. of body weight in a single dose. The techniques for administering these materials to animals are known to those skilled in the veterinary field.

Although the anthelmintic agents produced by the process of this invention find their primary use in the treatment and/or prevention of helminthiasis in domesticated animals, such as sheep, cattle, horses, dogs, swine and goats, they are also effective in treatment of helminthiasis that occurs in other living animals.

1. A compound which is 1-(n-octylthiocarbonyl)-2-(4-thiazolyl)-benzimidazole.

* * * * *